United States Patent [19]

Kilbourne

[11] 4,029,763

[45] June 14, 1977

[54] INFLUENZA VACCINE CONTAINING PURIFIED NEURAMINIDASE ANTIGEN AND METHOD OF USING THE SAME

[75] Inventor: Edwin D. Kilbourne, Ridgewood, N.J.

[73] Assignee: Mount Sinai School of Medicine of the City University of New York, New York, N.Y.

[22] Filed: Jan. 16, 1975

[21] Appl. No.: 541,512

Related U.S. Application Data

[63] Continuation-in-part of Ser. No. 494,716, Aug. 5, 1974, which is a continuation of Ser. No. 291,797, Sept. 25, 1972, abandoned.

[52] U.S. Cl. ................................................ 424/89
[51] Int. Cl.² ........................................ A61K 39/18
[58] Field of Search ...................................... 424/89

[56] References Cited

OTHER PUBLICATIONS

Schulman et al., J. Virol., vol. 2, pp. 778–786, Aug. 1968.
*Chemical Abstracts* (1), vol. 78, entry 93005d, 1973.
*Chemical Abstracts* (2), vol. 80, entry 81006h, 1974.
Dowdle, *New England J. Med.*, vol. 286, pp. 1360–1361, June 1972.
Kilbourne, *Hospital Practice*, Oct. 1971, pp. 103–114.
Kilbourne et al., *J. Virology*, vol. 2, pp. 281–288, Apr. 1968.
*The Lancet*, Aug. 5, 1972, pp. 264 & 265.
Rott et al., *J. Gen. Virol.*, Vol. 22, pages 35–41, 1974.
Schild, *J. Hyg. Camb.*, vol. 67, pp. 353–365, June 1969.

*Primary Examiner*—Sam Rosen
*Attorney, Agent, or Firm*—Brumbaugh, Graves, Donohue & Raymond

[57] ABSTRACT

An influenza vaccine is disclosed which comprises, as an active ingredient, a neuraminidase antigen which has been isolated from an antigenically functional virus and has substantial cross-reactivity with the influenza virus against which the vaccine is to be effective. The neuraminidase antigen can be derived from a virus antigenically representative of the contemporary or prevalent influenza virus subtype of interest, e.g., H3N2, the Hong Kong variant of influenza.

4 Claims, No Drawings

INFLUENZA VACCINE CONTAINING PURIFIED NEURAMINIDASE ANTIGEN AND METHOD OF USING THE SAME

This is a continuation-in-part of application Ser. No. 494,716 filed 8/5/74 which in turn is a continuation of application Ser. No. 291,797 filed 9/5/72 abandoned.

The present invention is directed to an influenza vaccine containing an antigenically functional and purified neuraminidase, freed of hemagglutinin protein, which forms the sole active component thereof, and a method of immunization using a vaccine.

The prior art has relied exclusively upon vaccines which comprise, an active component, viruses containing hemagglutinin and neuraminidase antigens which both have a substantial cross-reactivity with the type of virus against which the vaccine is to be effective. The term "cross-reactivity" as used herein refers to the ability of a given virus to produce antibodies which will inhibit challenge by another virus. When prior art vaccines are administered to an animal they produce antibodies in the animal which are effective against both surface antigens of the wild influenza virus. The use of such a vaccine protects the host animal against both infection and manifestation of symptoms of illness. However, the protection afforded when such prior art vaccines are used is quite transient for reasons that are not entirely clear to persons of skill in the art.

Various recombinant viruses are known and have been used as laboratory reagents to analyze human and animal sera for their antibody content. In addition, recombinant viruses which contain hemagglutinin and neuraminidase antigens which both have substantial cross-reactivity with the influenza virus which subsequently challenges immunity have been used to immunize animals, such as man, swine, horses and fowl. "Future Influenza Vaccines and the Use of Genetic Recombinants", Kilbourne, E. D., Bulletin of the World Health Organization, Vol. 41, pp. 643–645 (1969), "Correlated Studies of a Recombinant Influenza Virus Vaccine", The Journal of Infectious Diseases, Vol. 124, No. 5 (1971), and The New York Times, Aug. 13, 1972.

It is now well established that hemagglutinin and neuraminidase are antigenically distinct proteins of the envelope of influenza virus, and that by genetic recombination hybrid (recombinant) viruses can be produced in which hemagglutinin is derived from one parental virus, and neuraminidase from the other. Such antigenically hybrid viruses have proved useful in the isolation of neuraminidase free of demonstrable hemagglutinin protein and in the production of specific antibody to viral neuraminidase.

Although antigenically hybrid recombinants that effectively segregate neuraminidase from hemagglutinin antigens have been described, Laver and Kilbourne, Virology, Vol. 30, p. 500 (1966), it has not been recognized heretofore that long-term protection against influenza virus can be obtained by using, in a suitable influenza vaccine, isolated neuraminidase antigen having substantial cross-reactivity with that particular influenza virus of interest as the active ingredient. The use of such a mono- rather than bi- specific antigen in the vaccine allows the animal to become infected with the wild influenza virus with which it is challenged while protecting it against manifestations or symptoms of illness. The presence of such infection in the animal is believed to stimulate the nautral immunological response of that animal thereby aiding in giving long-term protection. The use of purified neuraminidase in studies of mice in order to compare the relative effectiveness of specific immunity to viral neuraminidase and immunity to viral hemagglutinin in protecting mice against challenge with influenza virus infection was reported on by Schulamn, Khakpour and Kilbourne, Virology, Vol. 2, pp. 778–786 (168).

The present invention is a influenza vaccine which comprises, as an active ingredient thereof, purified neuraminidase antigen having substantial cross-reactivity with the challenge influenza virus against which the vaccine is to be effective. When such a vaccine is administered only antibodies to the neuraminidase of the challenge virus are produced in any substantial amounts. Immunization of the host animal, i.e., those subject to naturally-occurring influenza, is performed by administering an effective amount of the vaccine containing the purified neuraminidase antigen of the desired influenza virus by any suitable route of administration, e.g., by intraperitoneal, subcutaneous or intramuscular injection. Also forming a part of the present invention is an antigenically functional virus derived from parental viruses which are non-neurovirulent and which contain a neuraminidase antigen which has substantial cross-reactivity with contemporary challenge influenza viruses.

The process for preparing the antigenically functional vaccine in which isolated neuraminidase antigen is the sole active ingredient is known in the art and described by Laver, Virology, Vol. 20, pp. 251–262 (1963) and Laver and Kilbourne, Virology, Vol. 30, pp. 493—501 (166). Basically the process involves disrupting samples of purified recombinant or parental viruses by treatment with sodium dodecyl sulfate (SDS), separating their protein components by electrophoresis on cellulose acetate and thereafter isolating the specific neuraminidase antigen which has substantial cross-reactivity with the type of virus against which the vaccine is to be effective.

A variety of possible viruses can be used as the source of the purified neuraminidase antigen depending upon the particular strain or strains of influenza virus against which the vaccine is to be effective. It is possible to use quite a few subtype viruses of Type A, or B influenza viruses. The HON1 and H1N1 subtypes, for example, are described in Bull, W.H.O.: 45, 119 (1971). For example, one of the viral parents used in the recombination step can be an influenza virus selected from influenza A subtypes including H0N1, H2N2 or H3N2 viruses. One particular virus of great importance at the present time in immunization work is the Hong Kong (HK) variant of influenza which is sometimes designated as the A/Hong Kong (H3N2) influenza virus.

A neuraminidase vaccine according to the present invention which is effective against the Hong Kong variant can be formulated by recombining an A₀ influenza virus, e.g., A/PR8/34 (HON1), with the Hong Kong variant, e.g., HK/Aichi/68 (H3N2), to form hybrid recombinants, some of which contain hemagglutinin and neuraminidase antigens which both have cross-reactivity with the type of influenza virus against which the vaccine is to be effective. Thereafter the neuraminidase antigen (N2) portion of the progeny, e.g., H3N2, is isolated according to procedure discussed above, said antigen having substantial cross-reactivity with the influenza virus against which the vaccine is to be effective. Such an antigen (eg. N2), after isolation, when used as an active component in a vaccine, will protect the host animal against the Hong Kong variant of influenza. If the vaccine is desired for use in man, the parent strains used in the initial recombination steps should be non-neurovirulent. The absence of neurovirulence in such viruses may be indicated by the inability of the viruses to produce plaques or virus colonies in a human conjunctival cell-culture system (clone 1-5C-4 cells; Sugira et al., Virology, Vol. 26, pp. 478–488 [1965]).

TABLE 1

Table 1 contains data which establishes the non-neurovirulence of the parental virus.

Comparative titration of X-32 (non-virulent) and X-15 (HK) (neurovirulent)* recombinant viruses in a human conjunctival cell line (clone 1-5C-4) (both viruses are antigentically identical, but X-15(HK) is derived from a neurovirulent grandparent).

| virus | dilution inoculated | plaque formation** | plaque titer |
|---|---|---|---|
| X-32 | $10^{-1}$ | 0 | $<10^{-1}$ |
|  | $10^{-2}$ | 0 |  |
|  | $10^{-3}$ | 0 |  |
|  | $10^{-4}$ | 0 |  |
|  | $10^{-5}$ | 0 |  |
| X-15 (HK) | $10^{-1}$ | + | $10^{-4.5}$ |
|  | $10^{-2}$ | + |  |
|  | $10^{-3}$ | + |  |
|  | $10^{-4}$ | + |  |
|  | $10^{-5}$ | 0 |  |

Conclusion: two antigenic hybrids, indistinguishable antigenically, but one potentially neurovirulent (i.e., with neurovirulence genes) can be distinguished on the basis of differing virulence in a human cell culture system.

The genealogy and derivation of these recombinant antigenically hybrid viruses is presented below:

Derivation of X-15 (HK) (Summary)

```
A₀/NWS/(MK)            X       HK/16/68
─────────────                ─────────────────
A/NWS/33(HON1)               A/HongKong/1/68(H3N2)
(neurovirulent)  │
                 A₀(E)HK       X      A/equil
                 ─────                ─────────
                 (HON2)               Heq1Neq1
                         │
                     X-15(HK)
                     ─────────
                     Heq1N2
```

Derivation of X-32 (Summary)

```
A₀/PR8/34***           X       HK/Aichi/68***
─────────────                ─────────────────
A/PR8/AnnArbor/34(HON1)      A/Aichi/68(H3N2)
                         │
                     X-31***       X      A/Eq/1
                     ─────                ─────────
                     H3N2                 Heq1Neq1
                                  │
                              X-32
                              ─────
                              Heq1N2
```

*potentially neurovirulent
**focal destruction and lesions of cell culture monolayers
***strain used in commercial vaccine production in USA The process used in the formation of recombinant viruses is a known procedure in the art and is described in a number of publications including the following: Kilbourne and Murphy, J. Exper. Med.: 111, 387 (1960); Kilbourne, Science, Vol. 160, April 5, 1968, pp. 74–75; and Laver and Kilbourne, Virology, Vol. 30, pp. 493–501 (166). It basically comprises inoculating chick embryo allantoic sacs with the two viruses which are to be recombined. The resultant hybrid progeny are hybrids of both parental viruses. Generally, a high yield, i.e., high growth potential, and a low yield virus will be used as parents. A portion of the hybridized progeny of the recombination step can be eliminated in a cloning step by adding an antibody which is specifically cross-reactive with the high-yield parental virus and hybrid progeny possessing the hemagglutinin of that parent. The remaining hybrid are then, if necessary, inoculated into further chick embryo allantoic sacs, and when removed, contain a higher percentage of virus of the desired antigenic composition. Diluting the viruses to high dilution values insures that the high yield virus progeny will outgrow those having the lower growth potential.

The dosage of the neuraminidase antigen that is administered to man is equivalent to that contained by whole viruses comprising 500 to 100 chick cell agglutinating units.

The present invention is further illustrated by the following examples:

EXAMPLE I

To produce the neuraminidase antigen used in the present invention neuraminidase is isolated in active form via an affinity column bearing an inhibitor specific for this component. The column, developed by Cuatrecasas and Illiano, Biochem. Biophys. Res. Cummun., 44: 178 (1971), is prepared by CNBr activation of agarose, additon of the tripeptide, gly-gly-tyr, and diazotization of the inhibitor, N-p-animophenyl oxamic acid. This column isolation technique was adapted for use with influenza virus by the addition of Triton X-100 to absorbing and eluting buffers, Bucher, Abstr. Amer. Soc. Microbiol, p. 215 (1973). The use of Triton X-100 both stabilizes and maintains the solubility of the neuraminidase. The dissociation step of the intact virions is important, if SDS alone is used as the dissociating agent, the neuraminidase is quickly inactivated on adjustment to a mildly acidic pH 5.0 even for the relatively hardly X-7 virus strain, If Triton X-100 is used as the disrupting agent alone, the NA does not dissociate from HA, although the NA retains its activity. The use of the two detergents in sequence (1% SDS at pH 7.0, then Triton X-100 to 10% concentration followed by adjustment to pH 5.0) insures that the virion will be fully dissociated by activity will remain. After dialysis of the viral protein preparation at pH 5.0, the neuraminidase is absorbed to the column with the absorbing, pH 5.0, buffer. All other proteins pass through the column unhindered. The neuraminidase is eluted with pH 9.1 buffer, generally in a peak with a center of about pH 7 (see Graph 1). All fractions are assayed for protein, Lowry et al., J. Biol. Chem. 193: 265 (1951), and for neuraminidase activity, Cassidy et al., Methods in Enzymology, Vol. 8, pp. 680–685 (1966). The neuraminidase purification shown in Graph 1 had resultant yields of 125% of the activity of the disrupted

GRAPH 1

AFFINITY CHROMATOGRAPHY OF X-7 NEURAMINIDASE

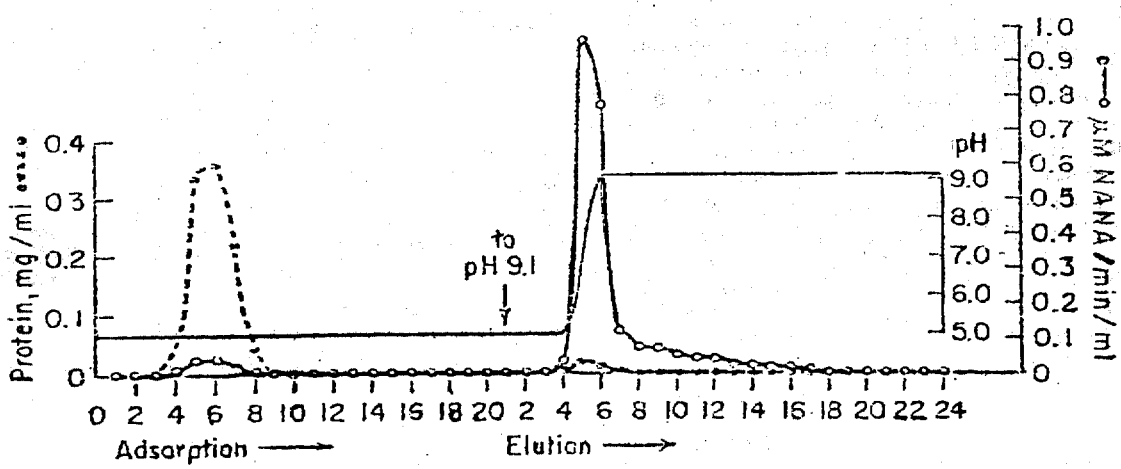

The viral preparation was disrupted as described in Table 2. Following dialysis overnight of the disrupted viral preparation versus pH 5.0 buffer containing 0.1% Triton X-100 at 4°, the sample was applied to the affinity column at room temperature. The column was washed with an additional 200 ml pH 5.0 buffer at a rate of 200 ml/hr. Fractions were collected in 10 ml aliquots with the aid of a fracton collector. The bulk of the protein elutes in tubes 4 through 8. The neuraminidase is eluated by elevation of the pH to 9.1. Fractions were assayed for protein (broken line, solid circles) and for neuraminidase activity (solid line, open circles). viral preparation associated with 1.6% of total protein. The protein recovery was 60.6%. The increase in specific activity was 77 fold. Results of the chromatogram of Graph 1 are summarized in Table 2. On polyacrylamide gel electrophoresis the neuraminidase migrated as a single high molecular weight component (molecular weight of about 250,000) when 10 µg material was applied to the gel, after a single cycle of purification. This procedure was also applied to a B strain (from an outdated lot of vaccine) and to a preparation of X-31. These strains, X-31 and B/Mass, have contaminating proteins accompanying then on the gels, at lower levels, but modifications of the disrupting technique should result in greater purity for these strains. It has been found that a second cycle on the affinity column after the addition of a relatively low level of reducer (0.01 M dithiothreitol) results in elimination of contaminating polypeptides for the X-31 and B strains. The methodology was elaborated primarily for the X-7 strain and found to work with other strains. Excellent recovery of active neuraminidase can be achieved at this step for all strains attempted including the very unstable $A_o$ neuraminidases.

EXAMPLE II

A vaccine was produced containing the purified neuraminidase antigen produced in Example I by inoculating chick embryo allantoic sacs with the diluted virus and harvesting the allantoic fluid after a two-day growth period. The allantoic fluid was preliminarily purified by low speed centrifugation which was followed thereafter by zonal ultracentrifugation to produce a semi-purified allantoic fluid virus. A product was produced consisting chiefly of purified influenza virus which was then subjected to disruption with detergents and affinity chromatography for the isolation of purified neuraminidase as described in Example I.

TABLE 2

PURIFICATION OF X-7 VIRAL NEURAMINIDASE BY AFFINITY CHROMATOGRAPHY

| | NA Activity | | Protein | | Specific Activity | Fold Purification |
|---|---|---|---|---|---|---|
| | Total Um NANA/min | % Yield | Total mg | % Yield | Um NANA/min/mg. | |
| SDS Disrupted X-7 Virus + Triton X-100 | 40.7 | — | 16.5 | — | 2.46 | — |
| Non-Adsorbed Virus Fraction (Protein-NA) | 2.46 | 4.7% | 10.0 | 60.6 | — | — |
| Enzyme Fraction (NA) | 49.9 | 123.0% | 0.264 | 1.6 | 189 | 77 |

EXAMPLE III

Immunization of mice with isolated X-7(F1) [N2] neuraminidase. Mice were injected subcutaneously with 0.3 ml of a mixture of equal parts of saline and complete Freund's adjuvant or of a 1:16 dilution of isolated N2 enzyme (E) derived from X-7(F1) (HON2) and adjuvant. The injections were repeated 40 days later, and 7 days after the booster injection three mice from each group were bled. Serum antibody levels were measured in HI tests against Jap. 305 (H2N2), X-7(F1) (HON2), X-9(H2N1), and X-15 (Heq1N2) viruses. Enzyme-inhibition titers were determined with X-7(F1) (HON2) virus, and plaque size-reducing titers were determined against X-7 (HON2) and NWS (HON1) viruses in clone 1-5C-4 human conjunctival cells (Table 3). Immunization of mice with E neuraminidase did not induce production of HI antibody against any of the viruses tested except X-15, but it did produce serum titers of 1:400 of enzyme-inhibiting antibody against X-7(F1) [N2] enzyme. In addition, the pooled sera of mice immunized with purified (E) enzyme had plaque size-reducing activity against X-7 virus (HON2) but not against NWS (Hon1) — a virsus that differs from the X-7 virus recombinant only in having a different neuraminidase protein (N1).

When groups of mice similarly immunized were challenged with Jap. 305 (H2N2) virus, the results given in Table 4 were obtained. Mice immunized with (E) neuraminidase had considerably lower pulmonary virus titers than control mice 2 and 4 days after Jap. 305 virus challenge; they had less extensive lung lesions 7 days after challenge.

TABLE 3

HI, enzyme inhibiting (EI), and plaque size-reducing (PSR) antibody response in mice immunized with purified N2 neuraminidase

| Immunization[a] | HI antibody titer | | | | EI titer[b] | PSR titer[c] | |
|---|---|---|---|---|---|---|---|
| | Jap. 305 H2N2 | X-9(A,e) H2N1 | X-7(F1) HON2 | X-15 Heq1N2 | X-7(F1) HON2 | X-7(HON2) | NWS(HON1) |
| Saline-adjuvant | <1:8 | <1:8 | <1:8 | <1:8 | <1:10 | <1:200 | <1:200 |
| Enzyme-adjuvant | <1:8 | <1:8 | <1:8 | 1:128 | 1:400 | 1:8,000 | <1:200 |

[a]Subcutaneous injection, 0.3 ml of a mixture of equal parts of saline and complete Freund's adjuvant or of a 1:16 dilution of purified X-7(f1) enzyme and Freund's adjuvant, 47 and 7 days prior to bleeding.
[b]Dilution of serum inhibiting 50% of neuraminidase activity of X-7(F1) virus.
[c]Final dilution of antiserum in agar overlay effective in reducing plaque size.

TABLE 4

Effect of immunization with isolated N2 neuraminidase on influenza Jap. 305 (H2N2) virus infection of mice

| | Pulmonary virus titers[b] | | Lung lesions (%) |
|---|---|---|---|
| Immunization[a] | Day 2 | Day 4 | Day 7 |
| Saline-adjuvant | 7.8 | 7.2 | 44.0 |
| Enzyme-adjuvant[a] | 5.5 | <3.7 | 5.0 |

[a]Subcutaneous injection as in Table 3.
[b]EID$_{50}$, log$_{10}$, five animals in each group. Enzyme = neuraminidase In addition, enzyme (N2) immunized and unimmunized mice were challenged with X-7(F1) (HON2), X-15 (Heq1N2), NWS (HON1), and X-9 (H2N1) viruses. Titers of pulmonary virus 3 days after challenge are given in Table 5. Significant reducts of pulmonary virus titers were observed when mice immunized with (N2) neuraminidase were challenged with viruses that contain (N2) enzyme [X-7(F1), X-15] but not when they were challenged with viruses that have an antigenically different neuraminidase (N1) protein, e.g., (NWS, X-9).

Thus, immunization of mice with isolated N2 neuraminidase resulted in enzyme-inhibiting serum antibody to N2 neuraminidase and, despite the lack of serum antibody reactive in hemagglutination-inhibition tests with any of the challenge viruses except X-15, led to significant protection against challenge infection with viruses containing N2 neuraminidase.

The code-named viruses used in forming the purified neuraminidase antigen and vaccine of the present invention can be obtained from the Bureau of Biological Standards of the Food and Drug Administration.

TABLE 5

Effect of immunizations with purified N2 neuraminidase on challenge infections with influenza viruses which do and do not contain N2 enzyme (E)

| | Pulmonary virus titers 72 hours after challenge[b] | | | |
|---|---|---|---|---|
| Immunization[a] | X-7(F1) (HON2) | NWS (HON1) | X-9 (H2N1) | X-15 (heq1N2) |
| saline-adjuvant | 5.1 | 6.8 | 6.0 | 6.7 |
| Enzyme-adjuvant | <2.1 | 7.0 | 6.4 | 4.4 |

[a]Subcutaneous injection as in Table 3.
[b]EID$_{50}$, log$_{10}$, five animals in each group.

A person of skill in the art upon reading the foregoing will become aware of a number of modifications which can be made to the invention described above without departing from the spirit and scope thereof. Hence, the foregoing is not to be taken as limiting since it is intended to be merely illustrative of a number of embodiments of the invention. The appended claims define the scope of protection sought.

I claim:

1. A method of influenza immunization comprising administering by injection to a human or an animal, subject to infection by natural means by naturally occurring influenza, an effective amount of a vaccine which comprises a purified neuraminidase antigen as essentially the sole functional component thereof, said antigen being substantially free from any hemagglutinin protein antigen and having substantial cross reactivity with a challenge natural contemporaneous or naturally infective wild type influenza virus, said antigen being derived from viruses which are not neurovirulent, the concentration of said antigen in said vaccine being sufficient to immunize the human or animal.

2. A method according to claim 1, wherein the neuraminidase antigen is derived from an influenza virus selected from the group consisting of a subtype of Type A or B influenza viruses.

3. A method according to claim 1, wherein the neuraminidase antigen is derived from the Hong Kong (H3N2) variant of Type A influenza virus.

4. A method according to claim 1, wherein the animal is man and the dosage of neuraminidase antigen that is administered is equivalent to that contained by whole virus comprising about 500 to 1000 chick cell agglutinating units.

* * * * *